(12) United States Patent
Ferrone et al.

(10) Patent No.: US 6,998,237 B1
(45) Date of Patent: Feb. 14, 2006

(54) GD3 PEPTIDE MIMICS

(75) Inventors: Soldano Ferrone, Buffalo, NY (US);
Xinhui Wang, Williamsville, NY (US);
Jeff Chi-Feng Hsu, Tonawanda, NY (US); Chun-Yen Tsao, Grand Island, NY (US); Wei Luo, Getzville, NY (US)

(73) Assignee: Health Research, Inc., Buffalo, NY (US)

( * ) Notice: Subject to any disclaimer, the term of this patent is extended or adjusted under 35 U.S.C. 154(b) by 107 days.

(21) Appl. No.: 10/618,336

(22) Filed: Jul. 11, 2003

Related U.S. Application Data

(60) Provisional application No. 60/395,232, filed on Jul. 11, 2002.

(51) Int. Cl.
*C12Q 1/68* (2006.01)
*A61K 38/04* (2006.01)
*C07K 16/00* (2006.01)

(52) U.S. Cl. .......................................... 435/6; 530/327

(58) Field of Classification Search ................ 530/300, 530/327, 328, 387.1; 424/184.1, 130.1
See application file for complete search history.

(56) References Cited

U.S. PATENT DOCUMENTS

| 5,807,978 A | 9/1998 | Kokolus et al. |
| 5,882,654 A | 3/1999 | Morton |

FOREIGN PATENT DOCUMENTS

| EP | 1279677 A1 * | 1/2003 |
| WO | WO 200038515 A1 * | 7/2000 |
| WO | WO 200181371 A1 * | 11/2001 |

OTHER PUBLICATIONS

Willers et al. (Peptides 1999; 20: 1021-1026).*
Chapman et al., *Vaccination with a Bivalent $G_{M2}$ and $G_{D2}$ Ganglioside Conjugate Vaccine: A Trial Comparing Doses of $G_{D2}$-Keyhole*, Clinical Cancer Research (Dec. 2000) vol. 6, pp. 4658-4662.
Grant et al., *Long Survival of Pateints with Small Cell Lung Cancer after Adjuvant Treatment with the Anti-Idiotypic Antibody BEC2 Plus Bacillus Calmette-Guérin*, Clinical Cancer Research (Jun. 1999) vol. 5, pp. 1319-1323.
Lesinski et al., *A DNA Vaccine Encoding a Peptide Mimic of Streptococcus Pneumoniae Serotype 4 Capsular Polysaccharide Induces Specific Anti-Carbohydrate Antibodies in Balb/c Mice*, Vaccine (2001) vol. 19, pp. 1717-1726.
Luo et al., *A Molecular Basis for Functional Peptide Mimicry of a Carbohydrate Antigen*, The Journal of Biological Chemistry (May 26, 2000) vol. 275, No. 21, pp. 16146-16154.
McCaffery et al., *Immunization of Melanoma Patients with BEC2 Anti-Idiotypic Monoclonal Antibody That Mimics GD3 Ganglioside: Enhanced Immunogenicity WhenCombined with Adjuvant*, Clinical Cancer Research (Apr. 1996) vol. 2, pp. 679-686.
Qiu et al., *Towards the Development of Peptide Mimotopes of Carbohydrate Antigens as Cancer Vaccines*, Hybridoma (1999) vol. 18, No. 1, pp. 103-112.
Yao et al., *Immunization of Melanoma Patients with BEC2-Keyhole Limpet Hemocyanin Plus BCG Intradermally Followed by Intravenous Booster Immunizations with BEC2 to Induces Anti-GD3 Ganglioside Antibodies*, Clinical Cancer Research (Jan. 1999) vol. 5, pp. 77-81.

* cited by examiner

*Primary Examiner*—Jeff Siew
*Assistant Examiner*—Brandon Fetterolf
(74) *Attorney, Agent, or Firm*—Hodgson Russ LLP

(57) ABSTRACT

The present invention provides peptide mimics for GD3 ganglioside. The peptide mimics were identified by panning phage display peptide libraries with an anti-GD3 monoclonal antibody. The peptide mimics inhibit the binding of an anti-GD3 antibody to GD3 positive cells and also elicit antibodies which can bind to GD3 positive cells. The identified peptide mimics can be used as immunogens for cancer therapy.

3 Claims, 5 Drawing Sheets

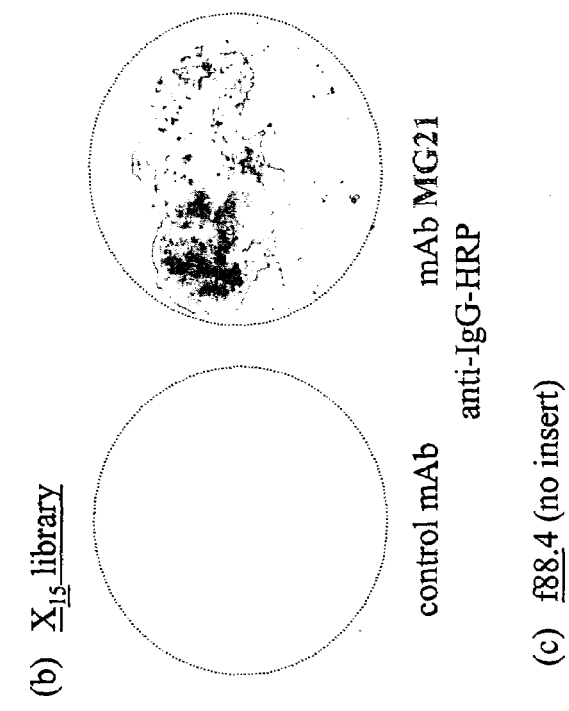
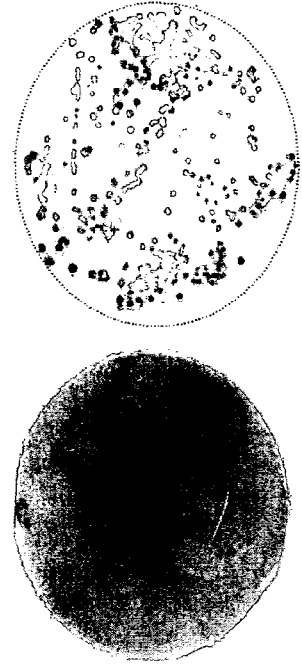
Figure 1b
(b) X_{15} library
(c) f88.4 (no insert)
Figure 1c
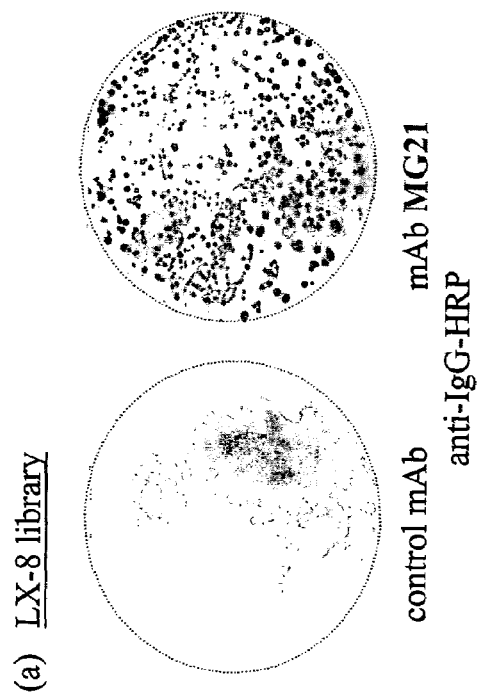
Figure 1a
(a) LX-8 library

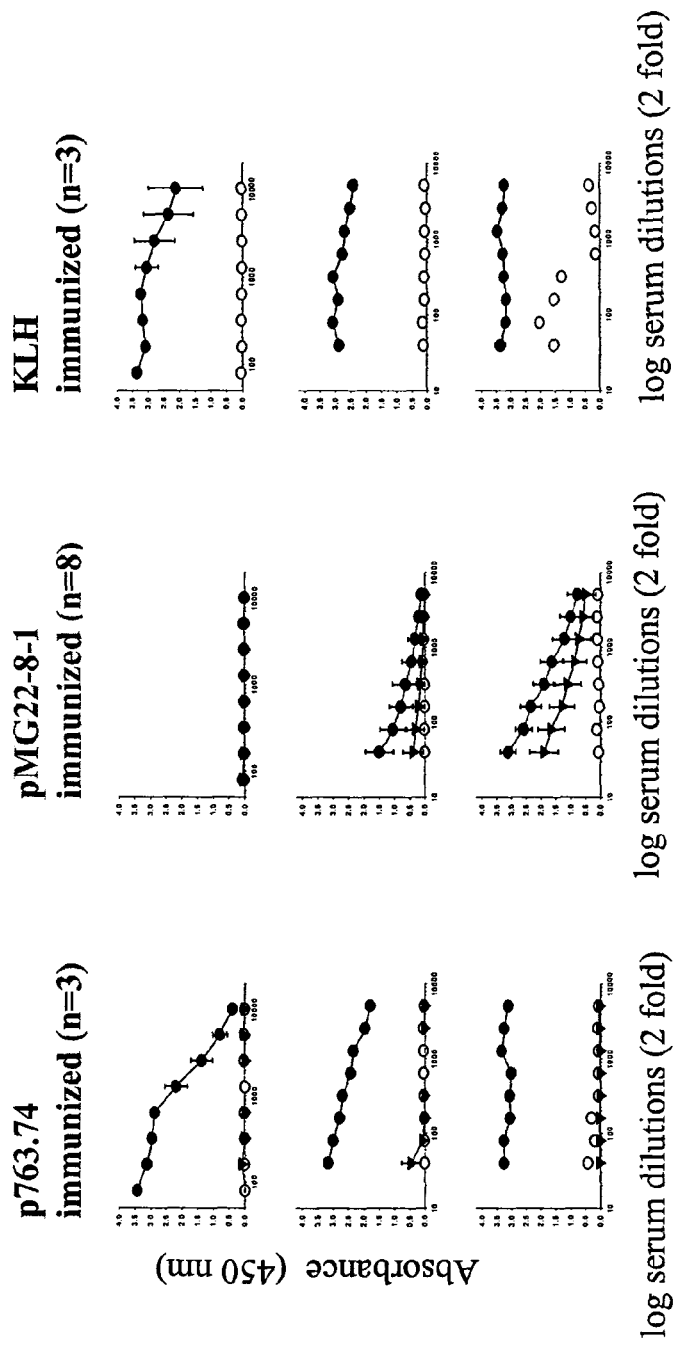

SEQUENCE LISTING

```
<160> NUMBER OF SEQ ID NOS: 7

<210> SEQ ID NO 1
<211> LENGTH: 12
<212> TYPE: PRT
<213> ORGANISM: artificial sequence
<220> FEATURE:
<223> OTHER INFORMATION: pMG21-8-1 peptide mimic for GD3

<400> SEQUENCE: 1

Asn Cys Ser Val His Ala Met Thr Pro Gly Cys Leu
                5                   10

<210> SEQ ID NO 2
<211> LENGTH: 12
<212> TYPE: PRT
<213> ORGANISM: artificial sequence
<220> FEATURE:
<223> OTHER INFORMATION: pMG21-8-2 peptide mimic for GD3

<400> SEQUENCE: 2

Asn Cys Asn Pro Tyr Thr Arg Val Asp Gly Cys Met
                5                   10

<210> SEQ ID NO 3
<211> LENGTH: 12
<212> TYPE: PRT
<213> ORGANISM: artificial sequence
<220> FEATURE:
<223> OTHER INFORMATION: pMG21-8-3 peptide mimic for GD3

<400> SEQUENCE: 3

Gln Cys Asp Pro Tyr Thr Arg Leu Glu Ser Cys Gly
                5                   10

<210> SEQ ID NO 4
<211> LENGTH: 12
<212> TYPE: PRT
<213> ORGANISM: artificial sequence
<220> FEATURE:
<223> OTHER INFORMATION: pMG21-8-4 peptide mimic for GD3

<400> SEQUENCE: 4

Arg Cys Pro Pro Glu Tyr Val Ala Ala Asp Cys Asp
                5                   10

<210> SEQ ID NO 5
<211> LENGTH: 15
<212> TYPE: PRT
<213> ORGANISM: artificial sequence
<220> FEATURE:
<223> OTHER INFORMATION: pMG21-15-1 peptide mimic for GD3
```

-continued

```
<400> SEQUENCE: 5

Gln Pro Phe Pro Cys Tyr Ser Asn Ala Pro Cys Gln Ser Pro Ser
                5                  10                  15

<210> SEQ ID NO 6
<211> LENGTH: 12
<212> TYPE: PRT
<213> ORGANISM: artificial sequence
<220> FEATURE:
<223> OTHER INFORMATION: pMG22-8-1 peptide mimic for GD3

<400> SEQUENCE: 6

Met Cys Pro Thr Asp Met Pro Ala Ser Leu Cys Met
                5                  10

<210> SEQ ID NO 7
<211> LENGTH: 20
<212> TYPE: DNA
<213> ORGANISM: artificial sequence
<220> FEATURE:
<223> OTHER INFORMATION: Primer

<400> SEQUENCE: 7
gccaatagta gcaccaacga                                              20
```

GD3 PEPTIDE MIMICS

This application claims priority of U.S. provisional application No. 60/395,232 filed on Jul. 11, 2002, the disclosure of which is incorporated herein by reference.

This work was supported by Grant no. CA 37959 from the National Institute of Health. The Government has certain rights in the invention.

FIELD OF THE INVENTION

This invention relates generally to the field of peptide mimics and more particularly to peptide mimics of gangliosides which can be used for immunotherapeutic approaches to malignancies such as melanoma and neuroblastoma.

BACKGROUND OF THE INVENTION

In America, lung cancer and melanoma are predicted to be the second and seventh most prevalent cancers for the year 2002, respectively (American cancer Society, Inc., 2002). Moreover, the all stage five-year relative survival rate between 1992–1997 for lung cancer in this country is only about 15%. On the other hand, although the five-year survival rate for all stage melanoma patients is relatively high at 89%, this rate drops sharply to approximately 12% when disease undergoes transformation into malignancy and metastasizes to distant sites in the body. Therefore, the low survival rates in these diseases call for newer cancer therapeutic approaches to be implemented.

In recent years there has been a growing interest in the development and application of active specific immunotherapy for the treatment of malignant diseases, in part due to the limited success of conventional therapy (see Giaccone et al., Cancer Chemotherapy and Biological Response Modifiers Annual 19, 2001). For developing tumor vaccines of melanoma, two major approaches have been used: 1) immunizations with whole tumor cell extracts or irradiated tumor cells (Takashi, et al. 1999; Hsueh, 2001); 2) immunizations with melanoma associated antigens such as MART-1 or gp100 (Chianese-Bullock, et al. 2002). Several researchers have considered the T cell and/or antibody-based immunotherapeutic approaches in patients with malignant diseases. The molecular characterization of T cell and/or antibody defined tumor associated antigen (TAA) has providded investigators with well-defined moieties to immunize patients with malignancies and to monitor the elicited immune response.

It has been reported that in humans, the large majority of tumor antigens are non-mutated self-antigens. They are likely to be expressed at a higher level by malignant cells than by normal cells because of systemic gene deregulation associated with the cell transformation process. Therefore development of strategies effective in inducing a strong immune response against self-TAA represents one of the major challenges facing immunologists.

One of the approaches used is the administration of anti-idiotypic antibodies. However, the majority of anti-idiotypic (anti-id) antibodies are of xenogenic origin, most being mouse monoclonal antibodies. As expected, administration of xenogenic anti-id antibodies induces high titer antibodies to the constant and variable regions of the immunizing antibody. Further, it has been reported that immunization with anti-id antibodies elicits humoral immunity, but not induced HLA class I antigen restricted TAA mimicty in most of the antigenic systems analyzed. In addition, it is also reported that there is low reactivity of the elicited antibodies with the original TAA. Accordingly, there continues to be need in the field of immunotherapy to develop novel approaches to stimulate an immune response against TAAs.

GD3 ganglioside is a self-glycolipid antigen highly expressed in human melanoma lesions and lung cancer cells compared to most normal tissues. Anti-GD3 monoclonal antibodies have been shown to effectively mediate lysis of GD3+ melanoma cells by complement and antibody-dependent mechanisms. Furthermore, antiGD3 monoclonal antibody may affect the biology of melanoma cells and can lead to inhibition of melanoma cell growth. These findings suggest that generation of immunity that specifically targets GD3 may have a beneficial effect on the clinical course of the disease by mediating destruction of GD3+ melanoma cells. However, development of active immunotherapy has been hampered by the unresponsiveness of patients' immune system to GD3.

In previous studies, peptide mimics have been generated and shown to induce specific immune responses against several antigens, including carbohydrate antigens such as Lewis antigens and S. pneumoniae serotype 4 capsular polysaccharide (Lesinski et al., 2001; Luo et al., 2000). In addition, clinical trials have already begun based on another kind of antigen mimic to GD3, an anti-idiotypic antibody BEC2 (Chapman et al., 1994; McCaffer et al., 1996; Yao et al., 1999). Immunization with BEC2 have been associated with induction of immune responses specifically targeted against GD3 in melanoma (Yao et al., 1999) and small cell lung cancer patients (Grant et al., 1999). Although GD2/GD3 peptide mimics have been isolated with an anti-GD2/GD3 antibody ME36.1, the antigenicity of these peptides was not demonstrated (Qiu et al., 1999), nor their ability to generate antisera that can bind to GD3 bearing cells. Accordingly, there continues to be a need to further identify and develop peptide mimics of tumor associated antigens useful for generating an immune response.

SUMMARY OF THE INVENTION

The present invention provides peptide mimics of the ganglioside GD3 and a method for producing same. This invention also provides a method of using the peptides to elicit an immune response against a tumor associated antigen that is not normally immunogenic.

Accordingly, in one aspect, the invention provides methods for identifying peptide mimics. The method comprises the steps of screening phage display peptide libraries with antibodies to GD3. The identified peptides are then tested for their ability to elicit an immure response and the reactivity of those antibodies against GD3 bearing cells.

In another aspect, the present invention provides a method for eliciting an immune response in patients with GD3 positive tumors. The method comprises administering a composition effective in stimulating a specific immunological response against the GD3 antigen. These composition(s) comprise a peptide that shares immunological characteristics of GD3. While a detectable immunological response is likely to be beneficial, efficacy can also be deduced by an improvement in symptoms or control of growth of the tumor.

Other aspects include methods for treating GD3 bearing tumors in an individual by eliciting an anti GD3 immunological response in the subject. The immunological response can be elicited using any of the peptide mimics to the GD3.

Still other embodiment include preparing a composition for use in the generation of an immune response and in the treatment of tumors bearing GD3. The composition comprises the peptide mimics disclosed herein.

BRIEF DESCRIPTION OF THE DRAWINGS

FIGS. 1a, 1b and 1c show specific binding of isolated phage particles to anti-GD3 monoclonal antibody in immunological screening. Following three rounds of panning with anti-GD3 mAb, isolated phage-transfected E. coli clones were blotted onto nitrocellulose membrane and tested for reactivity to anti GD3 mAb. Phage particles isolated with mAb MG21 from the LX-8 (FIG. 1a), and X15 (FIG. 1b) phage libraries bound specifically to this mAb. The vector f88.4 (FIG. 1c) was used as negative phage control. In 1a and 1b the high molecular weight-melanoma associated antigen-specific mAb 763.64 was used as a control.

FIGS. 4a, 4b, 4c are representations of induction of the anti-peptide and anti-carrier reponses. Mice were immunized on day 0, 14, 28 and 42. Sera was collected on day 10, 24 and 38. Results are shown for mice immunized with p763.74 (FIG. 4a), pMG22-8-1 (FIG. 4b) and KLH (FIG. 4c). Preimmune sera is indicated as -○-; reaction against the immunized peptide is indicated as -●-; and reaction against peptide not used for immunization is indicated as -Δ-.

FIG. 5b) and control peptide (p763.74; FIG. 5a).

DETAILED DESCRIPTION AND OPERATION

Figures 2A, 2B, 2C:
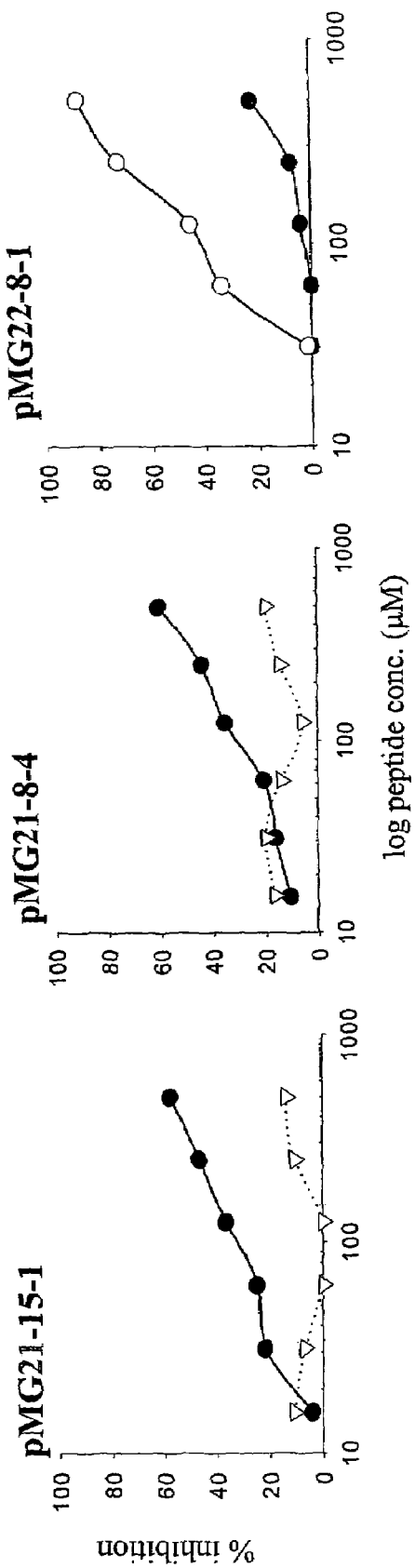
FIGS. 2a, 2b and 2c are representations of inhibition of binding of anti-GD3 monoclonal antibody to GD3+ cells by peptide mimics of the present invention. Data is shown for pMG21-15-1 (FIG. 2a), pMG21-8-4 (FIG. 2b) and pMG22-8-1 (FIG. 2c) for inhibition of binding of mAb MG22 (-○-); mAb MG21 (-●-) and mAb 763.74 (-Δ-).

The present invention is generally directed to peptide mimics of GD3 ganglioside which can be used in immunotherapy particularly for tumors bearing GD3 ganglioside. The method comprises administering to an individual in need of treatment, a composition comprising peptide mimics of GD3. While not intending to be bound by any particular theory, it is considered that the peptide mimics of GD3 as described herein will induce an immune response against the tumor-associated antigen GD3, which is usually not immunogenic. The peptide mimics of the present invention may be used for developing new active immunotherapy of malignancies such as melanoma and neuroblastoma.

Peptide mimics are structurally similar, but not identical, to GD3 ganglioside. Therefore, they may stimulate B cells with low affinities to GD3 ganglioside that survived from the regulation of self-reactive B cells during the establishment of self-identity. Furthermore, it is known that T cell-dependent responses are required to elicit long lasting antibody responses. However, immune responses to GD3 ganglioside are usually T cell-independent, due to lack of presentation of this glycolipid on HLA molecules. Because peptides can be presented on HLA molecules, peptide mimics are more likely to induce T cell-dependent immune responses than GD3 ganglioside. In addition, sequences of peptide mimics may also be utilized for the development of DNA vaccines.

The present invention seeks to overcome some of the drawbacks inherent in the prior art by identifying and isolating peptide/protein antigens that are highly immunogenic in humans. These antigens can then be used to promote specific anti-tumor responses. Peptide mimics have several advantages compared to other antigen mimics such as anti-idiotypic antibodies. First, the production of peptide mimics is easier to be standardized to meet the regulatory requirements for clinical trials. Second, immunization of peptide mimics avoids the induction of antibody responses to the irrelevant part of anti-idiotypic antibodies (Wang, et al. 2001). Third, modification and production of peptide mimics are easier than anti-idiotypic antibodies. This provides advantages when modifying peptide mimics to increase similarities between peptide mimics and GD3 ganglioside, or to increase the presentation of peptide mimics on HLA molecules. Fourth, peptide mimics isolated using different anti-ganglioside antibodies can provide the possibility of generating multiple antigen peptides (MAP), which may induce immune responses against multiple epitopes on GD3 ganglioside or even different TAAs. Fifth, peptide mimics can eliminate side effects due to the infusion of antibodies to patients. Finally, peptide mimics and their sequences can be used to develop dendritic-cell vaccines or DNA vaccines to GD3 ganglioside (Lesinski, et al. 2001). Furthermore, immunogenicity and half life of peptide mimics can be improved by constructing a MAP containing both B and T cell epitopes, or conjugating the peptide to a carrier protein such as KLH (Regenmortel, 2001).

While not intending to be bound by any particular theory, a proposed mechanism of action of the peptide mimics is as follows. Our hypothesis predicts that there exists a particular (combination of) amino acid sequences that allow the formation of a peptide structure which can mimic an epitope of a TAA. We further consider that, because the peptide mimics are similar but not identical to the original antigen, they are capable of inducing immune responses that may cross-react with the original TAA and in doing so, may reverse the unresponsiveness toward the original TAA.

As used herein, the term "peptide" refers to linear or cyclic or branched compounds containing amino acids, amino acid equivalents or other non-amino groups, while still retaining the desired functional activity of a peptide. Peptide equivalents can differ from conventional peptides by the replacement of one or more amino acids with related organic acids such as p-aminobenzoic acid (PABA), amino acid analogs, or the substitution or modification of side chains or functional groups. Peptide equivalents encompass peptide mimetics or peptidomimetics, which are organic molecules that retain similar peptide chain pharmacophore groups as are present in the corresponding peptide. The term "peptide" refers to peptide equivalents as well as peptides.

It is to be understood that limited modifications can be made to a peptide without destroying its biological function.

Thus, modifications of the peptides of the present invention that do not completely destroy their ability to generate anti-GD3 antibodies are within the definition of the compound claims as such. Modifications can include, for example, additions, deletions, or substitutions of amino acid residues.

As used herein, the term "cyclic peptide" refers to a peptide having an intramolecular bond between two non-adjacent amino acids. The cyclization can be effected through a covalent or non-covalent bond. Intramolecular bonds include, but are not limited to, backbone to backbone, side-chain to backbone and side-chain to side-chain bonds.

Specific peptides of the present invention can be isolated by a variety of methods based on their ability to bind to Anti-GD3 antibodies. For example, peptides characterized by specific anti-GD3 binding activity may be identified by screening a large collection, or library, of random linear peptides or cyclic peptides of interest. Cyclic peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with its encoding nucleic acid.

Screening phage-displayed random peptide libraries offers a rich source of molecular diversity and represents a powerful means of identifying peptide ligands that bind a receptor molecule of interest. For example, peptides are expressed on the tip of the filamentous phage M13, as a fusion protein with the phage surface protein pilus (at the N-terminus). Typically, a filamentous phage carries on its surface 3 to 5 copies of pili and therefore of the peptide. In such a system, few structural constraints are imposed on the N-terminus allowing the peptide to adopt many different conformations. However, biases in the distribution of peptides in the library may be caused by biological selection against certain of the peptides, which could reduce the diversity of peptides contained in the library.

Phage expressing binding peptides are selected by affinity purification with the target of interest. This system allows a large number of phage to be screened at one time. Since each infectious phage encodes the random sequence expressed on its surface, a particular phage, when recovered from an affinity matrix, can be amplified by another round of infection. Thus, selector molecules immobilized on a solid support can be used to select peptides that bind to them. This procedure reveals a number of peptides that bind to the selector and that often display a common consensus amino acid sequence. Biological amplification of selected library members and sequencing allows the determination of the primary structure of the peptide(s).

Peptide ligands identified by phage display screening frequently interact with natural binding site(s) on the target molecule, and often resemble the target's natural ligand(s). Although this system has been most often used to identify peptide epitopes recognized by antibodies, it has also been successfully used to find peptide mimics of carbohydrate molecules. The demonstrated ability of a peptide to mimic a carbohydrate determinant indicates that, although mimicry is accomplished using amino acids in place of sugars, the specificity pattern can be maintained.

Many phage display peptide libraries are known to contain more than $10^9$ different peptides in each library (Scott, et al. 1990; Bonnycastle, et al. 1996). A peptide that binds to the antigen recognition site of the antibody is expected to have a 3D structure similar to the original antigen. By panning a phage display peptide library with anti-GD3 ganglioside mAb, GD3 ganglioside peptide mimics, which specifically bind to the anti-GD3 ganglioside mAb can be isolated. Phage display peptide libraries have been shown to be useful in isolating peptide mimics of many different antigens, such as GD1á ganglioside (Ishikawa, et al. 1998), Lewis antigens (Luo, et al. 1998; Qiu, et al. 1999), MUC1 (Apostolopoulos, et al. 1999), E-selectin ligand (Fukuda, et al. 2000), anti-HER2/neu antibody (Park, et al. 2000), and capsular polysaccharide from *Streptococcus pneumoniae* (Lesinski, et al. 2001).

Methods for the production of phage display libraries, including vectors and methods of diversifying the population of peptides which are expressed, are well known in the art. (See, for example, Smith and Scott, Methods Enzymol. 217: 228–257 (1993); Scott and Smith, Science 249: 386–390 (1990); and Huse, WO 91/07141 and WO 91/07149). Cyclic peptide libraries also are well known in the art (see, for example, Koivunen et al., Methods Enzymol. 245: 346–369 (1994)). These or other well known methods can be used to produce a phage display library, from which peptides of the invention can be isolated using a variety of assays for binding to Anti-GD3 antibodies. Other methods for producing GD3 peptide mimics include, for example, rational design and mutagenesis.

Peptide mimics of GD3 ganglioside can be isolated by panning phage display peptide libraries with anti-GD3 ganglioside such as mAbs MG21 and MG22 that recognize different epitopes on GD3 ganglioside. Anti-GD3 ganglioside mAbs can be used to isolate phage that display antibody reactive peptides. After phage panning, the binding ability of isolated phage colonies to anti-GD3 ganglioside mAbs is tested with immunoscreening and further confirmed by ELISA. Anti-GD3 antibody reactive phage clone and the same phage without displaying peptides, can be utilized as a positive and a negative controls respectively in the immunoscreening and ELISA. In the positive phage clones, the DNA inserts that encode the antibody reactive peptides can be sequenced. Peptides can be synthesized based on the sequences of the DNA inserts. The synthesized peptides are tested in ELISA to determine their binding reactivity with corresponding anti-GD3 ganglioside mAbs. The ability of synthetic peptides to inhibit the binding of anti-GD3 ganglioside mAbs to GD2 ganglioside can be tested in an inhibition assay with GD3-positive cell lines. The synthetic peptides that inhibit or block the binding of anti-GD3 ganglioside mAbs to GD2 g angioside can be tested as active immunotherapy candidates.

Panning phage display peptide libraries (such as LX-8 and X15) with anti-GD3 ganglioside mAbs can be performed by routine procedures. For example, panning can be performed in 96-well microtiter plates (Falcon, Becton Dickinson, Lincoln Park, N.J.) as described previously (Bonnycastle, et al. 1996). A suitable amount of anti-GD3 ganglioside mAbs (0.5–5 µg/well) can be immobilized on an anti-mouse IgG (1+2a+2b+3) Fc' fragment coated 96-well microtiter plate. Phage display peptide libraries ($10_{12}$ virions/well) can be added to the anti-GD3 ganglioside mAb coated plates and incubated for a suitable period of time to effect specific binding (4° C. for 4 hours). After the incubation, the bound phage can be eluted. The eluted phage is incubated in wells coated with anti-mouse IgG (1+2a+2b+3) Fc' fragment antibody at 4° C. for an additional 1–2 hours to eliminate phage that bind to the anti-mouse IgG antibody. Phage in the supernatant can be amplified (in *E. coli* K91kan prepared as described by Smith, et al. 1993) and used for subsequent rounds of panning. Phage enrichment after each round of panning can be determined by spot titering on NZY plates containing tetracycline (20 µg/ml), as described by Smith and Scott (Smith, et al. 1993).

The binding ability of phage clones isolated following subsequent rounds of panning with anti-GD3 ganglioside mAbs can be examined by immunoscreening (Valadon, et al. 1996) with labeled (biotinylated) anti-GD3 ganglioside mAb. The binding activity of positive phage clones to anti-GD3 ganglioside mAbs can also be confirmed by ELISA. The procedures of immunoscreening are known to those skilled in the art (see Christian, et al. 1992). Briefly, phage clones on NZY plates can be transferred onto nitrocellulose membranes. The nitrocellulose membranes are incubated with labeled (biotinylated) anti-GD3 ganglioside mAbs in a suitable buffer (TNT7.5 buffer and 20% FCS for 2 hours). The membranes are washed and then incubated with a detecting agent (such as horseradish peroxidase (HRP)-conjugated streptavidin for 30 minutes). After incubation, antibody bound phage clones can be detected by standard methods. Positive phage clones identified by immunoscreening can be cultured in multi-well plates. The phage supernatants can be collected and subjected to ELISA.

For sequencing of the DNA inserts from phage clones reacting with anti-GD3 ganglioside mAbs, double stranded DNA is extracted by using commercially available kits (QIA prep. Spin, Miniprep kit, Qiagen Inc., Valencia, Calif.) from phage infected $E.$ $coli$ culture. The DNA sequencing can be performed with suitable primers (such as 5'-GCCAATAG-TAGCACCAACGA-3' (SEQ ID NO:7), which is complementary to the synthetic pVIII gene and locates at more than 90 bp. downstream of the DNA inserts). DNA sequencing is carried out by standard techniques.

Peptides identified according to this invention can be tested for their ability to bind to anti-GD3 antibodies and to generate anti-GD3 antibodies. The peptides of the present invention can be synthesized using methods well known in the art. Such methods include recombinant DNA methods and chemical synthesis. Recombinant methods of producing a peptide through expression of a nucleic acid sequence encoding a peptide in a suitable host cell are well known in the art, such as is described in Sambrook et al., Molecular Cloning: A Laboratory Manual, 2nd Ed, Vols 1 to 3, Cold Spring Harbor, N.Y. (1989), which is incorporated herein by reference.

Peptides of the invention can also be produced by chemical synthesis, for example, by the solid phase peptide synthesis of Merrifield (Merrifield et al., J. Am. Chem. Soc., 85:2149 (1964), incorporated herein by reference). Standard solution methods well known in the art also can be used to synthesize a peptide of the present invention (see, for example, Bodanszky, M., Principles of Peptide Synthesis (Springer-Verlag, 1984), which is incorporated herein by reference). Newly synthesized peptides can be purified, for example, by high performance liquid chromatography (HPLC), and can be characterized using, for example, mass spectrometry or amino acid sequence analysis.

A newly synthesized linear peptide can be cyclized by the formation of a bond between reactive amino acid side chains. For example, a peptide containing a cysteine-pair, or any of the cysteine analogs can be synthesized, and a disulfide bridge can be formed by oxidizing the peptide with 0.01 M $K_3Fe(CN)_6$ at pH 8.4. Alternatively, a lactam, a lysinonorleucine or a dityrosine bond can be formed. Methods for forming these and other bonds are well known in the art and are based on well established principles of chemical reactivity (Morrison and Boyd, Organic Chemistry, 6th Ed. (Prentice Hall, 1992).

A peptide of the present invention also can be cyclized by forming a peptide bond between non-adjacent amino acid residues as described, for example, by Schiller et al., Int. J. Pept. Prot. Res. 25:171 (1985), which is incorporated herein by reference. Peptides can be synthesized on the Merrifield resin by assembling the linear peptide chain using Nα-Fmoc-amino acids and Boc and tertiary-butyl proteins. Following release of the peptide from the resin, a peptide bond can be formed between the amino and carboxyl termini.

The peptide mimics of the present invention can be used for therapeutic purposes. More specifically, the therapeutic method generally referred to herein could include methods for the treatment of various malignancies or other pathologies associated with GD3 expressing cells by the administration of pharmaceutical compositions that comprise the mimic peptide(s), variants, analogs or active fragments thereof, effective inhibitors or enhancers of activation of the mimic peptide(s), or other equally effective drugs developed for instance by a drug screening assay prepared and used in accordance with a further aspect of the present invention. For example, the mimic peptide(s) of the present invention, variants, analogs or active fragments thereof, as particularly represented by any of SEQ ID NOS: 1–6 may be administered to inhibit the growth of GD3 expressing tumors.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The proteins may also be incorporated into Immune Stimulating Complexes together with saponins, for example Quil A (ISCOMS).

Immunogenic compositions used to raise antibodies comprise a 'sufficient amount' or 'an immunologically effective amount' of the peptides of the present invention, as well as any other of the above mentioned components, as needed. 'Immunologically effective amount', means that the administration of that amount to an individual, either in a single dose or as part of a series, is effective to provoke an immune response and to raise antibodies, as defined above. This amount varies depending upon the health and physical condition of the individual, the taxonomic group of the individual to be treated (e.g. nonhuman primate, primate, rabbit, etc.), the capacity of the individual's immune system to synthesise antibodies, the immunogenicity of the antigenic peptide, and its mode of administration, and other relevant factors. It is expected that the amount will fall in a relatively broad range that can be determined through routine trials. Usually, the amount will vary from 0.01 to 1000 mg/dose, more particularly from 0.1 to 100 mg/dose. Subsequent to initial administration, individuals may be boosted by readministration. In some preferred embodiments, multiple administrations are performed.

The immunogenic compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The immunogenic compositions may be administered in conjunction with other immunoregulatory agents.

For parenteral administration, the compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in Remington's Pharmaceutical Sciences (18th Edition, A. R. Gennaro et al. Eds., Mack Publishing Co., Easton, Pa., 1990), a standard reference text in this field. A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

Peptide mimics of GD3 have numerous advantages over immunotherapies based on monoclonal antibodies or anitidiotypic antibodies. First, peptide mimics can eliminate side effects due to the infusion of antibodies to patients. Second, peptide mimics are easier to be modified according to different purposes such as increasing the binding of peptides to MHC complex. Last but not least, peptide mimics can induce active (memory) immune responses with longer duration than passive monoclonal antibody therapies.

The peptide mimics of the present invention can be used as immunogens in cancer therapy such as in melanoma, neuroblastoma or lung cancers. The therapy may be initiated at any time during the treatment of disease. The peptides may also be used for treatment of recurrent tumors.

The following examples are presented to further illustrate this invention. These examples are intended to be illustrative and should not be construed as limiting.

EXAMPLE 1

Identification of Peptide Mimics

Two monoclonal antibodies MG21 and MG22 to GD3 were tested by "biopanning" against two phage display libaries pVIII LX8 and pVIII X15. For each round of phage selection, 8 µg of either antibody were immobilized by equal amounts (by weight) of pre-coated goat anti-mouse IgG. Following a two-hour incubation (room temperature) with 5% non-fat dry milk, 10 mM EDTA Tris buffered saline solution, $10^{12}$ virions from pVIII LX8 or pVIII X15 were added to the solution. This mixture was incubated for four hours (4° C.) and then washed six times with Tris Buffered Saline to remove the unbound phages.

The bound phages were eluted by a ten-minute incubation with an acidic solution (0.1 M Hydrochloric acid, pH 2.2) followed by pH neutralization with an alkaline solution (1 M Tris, pH 9.1). The phage-containing eluant was used to transform $2.5 \times 10^7$ mid log phase K91kan (E. coli) cells in super broth solution (bactotryptone, yeast extract, NaCl) containing 15 µg/ml tetracycline (18–20 hours, 250 rpm, 37° C.). Surviving clones contained phage-incorporated tetracycline resistance genes. The phage-infected K91 kan culture solution was then centrifuged (4000 rpm, 30 min) and the supernatants collected. Half of the supernatant was used for subsequent rounds of selection and half stored in −20° C. (50% glycerol) for future use.

After the third biopanning, phage-infected K91kan culture supernatants from this panning were plated (in 10× dilutions) onto NZY agar plates containing 100 µg.ml tetracycline. Presence of positive phage clones on these plates was examined by "immunoscreening" and "reverse ELISA" procedures.

Briefly, for immunoscreening (FIG. 1), the plates were overlaid with dry nitrocellulose filters and then reacted with MG21 or MG22, followed by reaction with horseradish peroxidase (HRP)-conjugated goat anti-mouse IgG. After washing, filters were developed by chemiluminescence. If presence of MG21- or MG22-binding phage clones were detected, each (positive) clone on the plates was then isolated and cultured in NZY medium (20 h, 150 rpm) for further testing with reverse ELISA. For reverse ELISA, monoclonal K91kan-phage culture supernatants were reacted with pre-immobilized MG21 or MG22 followed by reaction with HRP-conjugated mouse anti-M13. Optical density (OD) measurements at 450 nm were done after 10 min of incubation in the presence of HRP substrate (TMB). Positive phage clones were identified based on OD comparisons between phage supernatants reacted with MG21 or MG22 and that reacted with an irrelevant antibody. The data obtained is shown in Table 1.

TABLE 1

Reactivity of Isolated Phage Clones to Anti-GD3 mAb in Reverse ELISA

| MAb | No. of clones screened | No. of anti-GD3 mAb reactive clones |
|---|---|---|
| MG21 | | |
| LX8 Library | 82 | 82 |
| X15 Library | 91 | 3 |
| MG22 | | |
| LX8 Library | 96 | 93 |
| X15 Library | 67 | 0 |

For further characterization, the pVIII gene inserts of positive phage clones identified by reverse ELISA were sequenced. Peptides encoded by these sequences were synthesized and then tested for GD3 specificity. This was done by assessing the peptides' ability to compete with MG21 or MG22 for binding to GD3-bearing melanoma cell line in vitro. Those peptides that significantly inhibited binding of MG21 or MG22 to the melanoma cells were considered as peptide mimics.

The following peptide mimics were isolated using the method described above. SEQ ID Nos: 1–4 and 6 were isolated from LX-8 phage library while SEQ ID NO: 5 was isolated from X15 phage library.

| Peptide Mimics isolated using MG21 | |
|---|---|
| pMG21-8-1 | NCSVHAMTPGCL - SEQ ID NO:1 |
| pMG21-8-2 | NCNPYTRVDGCM - SEQ ID NO:2 |
| pMG21-8-3 | QCDPYTRLESCG - SEQ ID NO:3 |
| pMG21-8-4 | RCPPEYVAADCD - SEQ ID NO:4 |
| pMG21-15-1 | QPFPCYSNAPCQSPS - SEQ ID NO:5 |

Peptide Mimics isolated using MG22 pMG22-8-1 MCPTDMPASLCM—SEQ ID NO:6

EXAMPLE 2

This embodiment demonstrates that the peptide mimics identified as described in Example 1 inhibit the binding of anti-GD3 monoclonal antibodies to GD3+ cells. Cyclized pMG21-15-1, pMG21-8-4 and pMG22-8-1 were tested for inhibiting the binding of the anti-GD2 mAb to Melur melanoma cells. The results are shown in FIG. 2 (a–c). The peptides inhibited in a specific and dose-dependent manner the binding of their respective panning mAbs.

EXAMPLE 3

Figure 3:
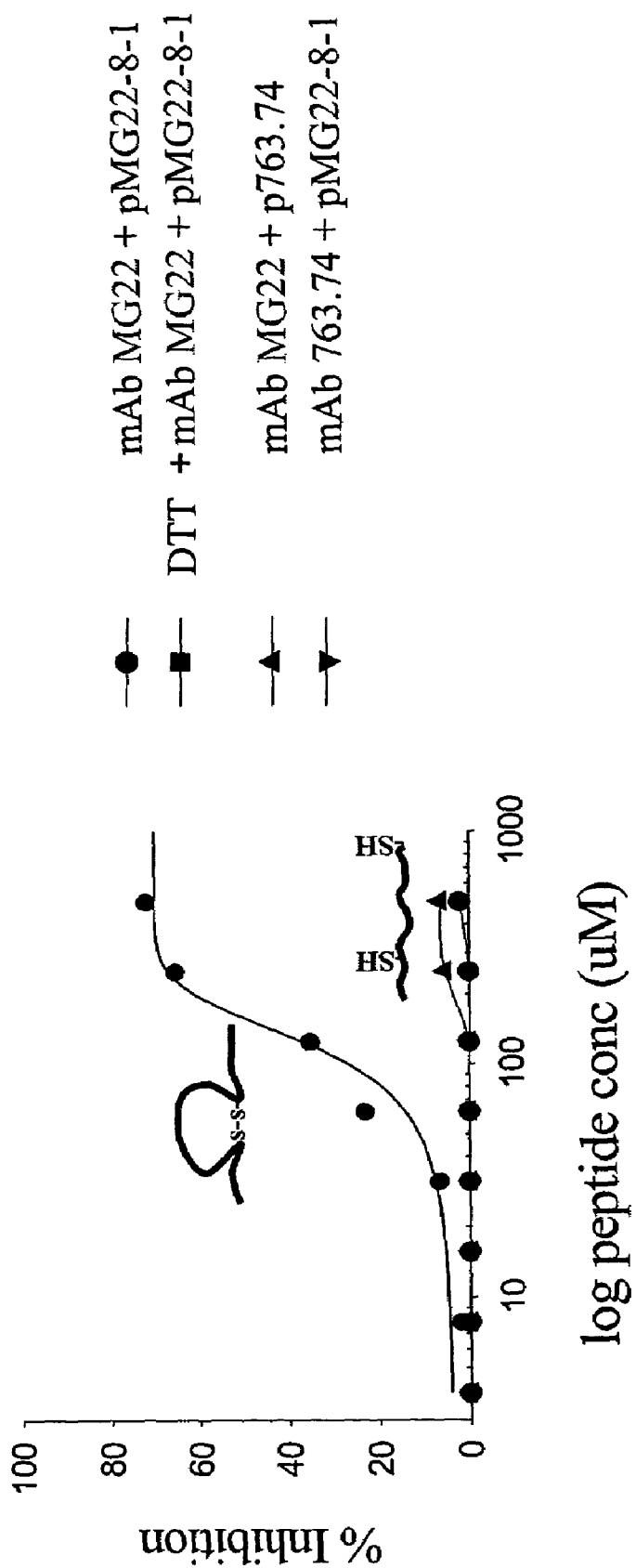
FIG. 3 is a representation of the effect of dithiothrietol (DTT) on inhibition of MG22 binding to GD2/3+Melur cells by pMG22-8-2. The peptide mimic pMG22-8-1 is able to inhibit binding of MG22 to Melur cells in a dose-dependent manner (up to 72% inhibition at 500 μM). This inhibitory effect was abolished by the pre-incubation of pMG22-8-1 with 10 mM DTT (—SH), confirming that the inhibitory peptide was in its cyclized form (-S-S-). 763.74, a monoclonal antibody that recognizes another melanoma-associated antigen—the High Molecular Weight-Melanoma Associated Antigen (HMW-MAA), is used here as an irrelevant antibody to show the binding specificity of GD2/3 peptide mimic pMG22-8-1 for mAb MG22; and p763.74 is a HMW-MAA peptide mimic isolated using the mAb 763.74. It is used here as an irrelevant peptide mimic to show the binding specificity of the GD3-specific mAb MG22 for pMG22-8-1.

This embodiment demonstrates that the peptide mimics of the present invention may be effective in their cyclized forms. The effect of 10 mM DTT on the inhibition of binding of anti-GD3 mAb to GD3+ cells was investigated. As shown in FIG. 3, DTT abolished pMG22-8-1 mediated inhibition of mAb MG22 binding to GD3+ cells suggesting that the inhibitory activity of this peptide was mediated in its cyclized form.

EXAMPLE 4

This embodiment demonstrates the induction of anti-peptide antibodies. Mice were immunized with pMG22-8-1, p763.74 peptides or KLH. Sera was tested on day 10, 24 and 38. As shown in FIGS. 4a, 4b and 4c, sera from all immunized mice developed high titer of antibodies reacting to GD3 peptide mimic pMG22-8-1, control peptide (763.74) and the carrier (KLH). In the group immunized with pMG22-8-1, the titer of antibodies reacting against the GD3 peptide mimic is observed. Also observed was an increase in non-specific antibodies as seen by an increase in the titer of antibodies reacting to p763.74 (FIG. 4b).

EXAMPLE 5

Figures 5A, 5B:
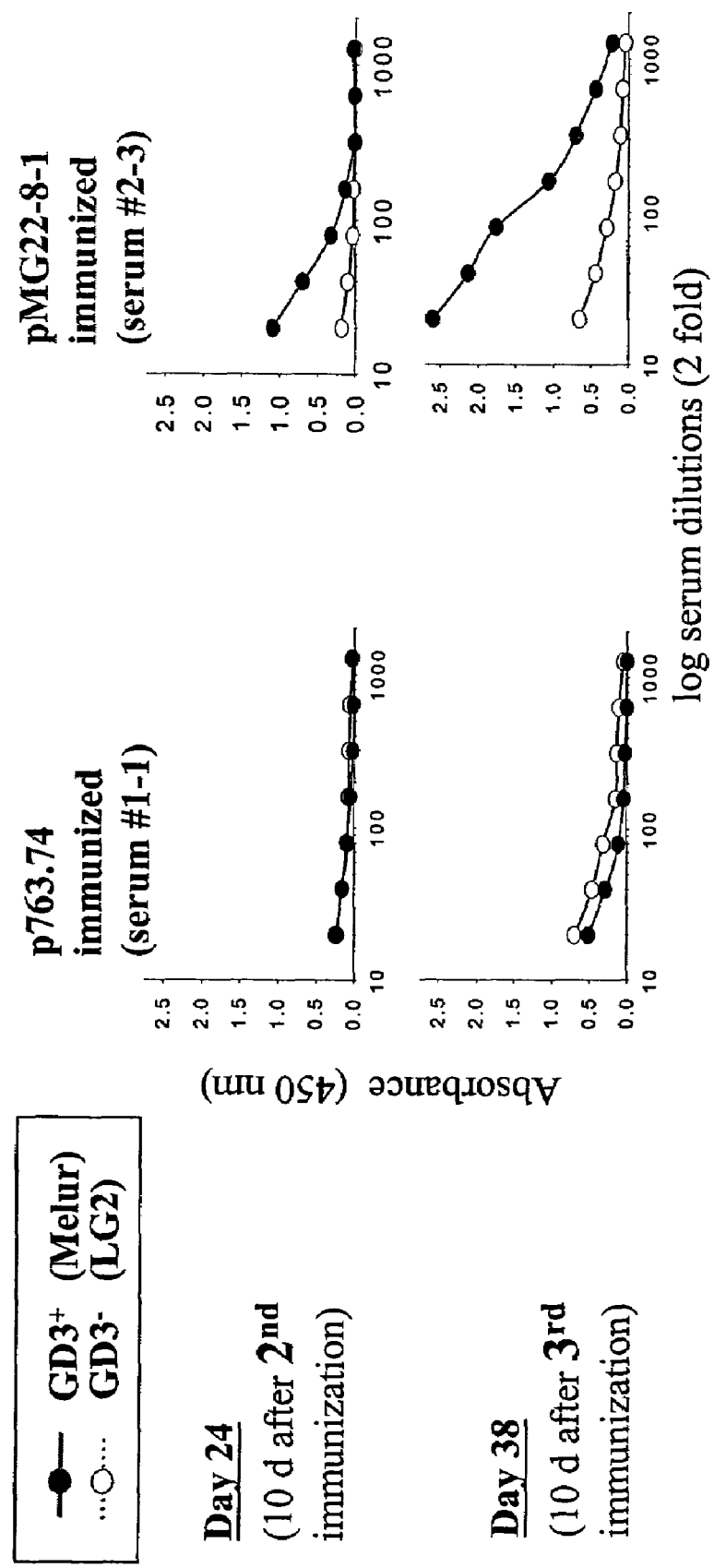
FIGS. 5a and 5b are representations of the selective reactivity of sera from mice immunized with GD3 peptide mimic pMG22-8-1. Immunizations were carried out on day 1, day 14, day 28 and day 42. Serum samples were collected on day 24 and day 38 and tested for binding to GD3 positive or negative cells. Results are shown for a peptide mimic according to the present invention (pMG22-8-1.

This embodiment demonstrates the generation of GD3 specific antibodies upon immunization of animals with the peptides of the present invention. Mice were immunized with peptide pMG22-8-1 (SEQ ID NO:6) on days 0, 14, 28 and 42. Sera was collected on days 24 and 38. The sera was tested for reactivity to GD3 positive (Melur) cells compared with GD3 negative cells (LG2) by ELISA. As shown in FIG. 5 (a, b), following two immunizations, serum from one out of eight mice (serum #2–3) immunized with the peptide of SEQ ID NO:6 reacted selectively to GD3 positive cell line (FIG. 5b). Sera obtained form none of the other seven mice in the same group nor six other mice immunized with either control peptide (FIG. 5a) or carrier protein KLH (data now shown) displayed selective reactivity to GD3 bearing cells.

These data demonstrate that the peptide mimics of the present invention inhibit the binding of anti-GD3 antibodies to GD3 expressing cells and that immunization of animals with the peptide mimics generates antibodies which specifically bind to GD3 expressing cells.

From the foregoing, it will be appreciated that although specific embodiments of the present invention have been described for the purposes of illustration, various modifications may be made without deviating from the spirit and scope of the invention.

REFERENCES

1. American Cancer Society: Cancer Facts & Figures 2002 (2002), American Cancer Society, Inc.
2. Apostolopoulos, V., Sandrin, M. S., and McKenzie, I. F. Carbohydrate/peptide mimics: effect on MUC1 cancer immunotherapy. J. Mol. Med. 77:427–436, 1999.
3. Bonnycastle, L. L., Mehroke, J. S., Rashed, M., Gong, X. and Scott, J. K. Probing the basis of antibody reactivity with a panel of constrained peptide libraried displayed by filamentous phage. J. Mol. Biol. 258:747–762, 1996.
4. 4. Chapman, P. B., Livingston, P. O., Morrison, M. E., Williams, L., Houghton, A. N. (1994). Immunization of melanoma patients with anti-idiotypic monoclonal antibody BEC2 (which mimics GD3 ganglioside): Pilot trials using no immunological adjuvant. Vaccine Res. 3, 59–69.
5. Chianese-Bullock, K. A. and Slingluff, C. Peptide vaccines for cancer. In: Principles and practice of biologic therapy of cancer (update). 3: 1–16, 2002. Rosenberg, S. A. edit.
6. Christian, R. B., Zuckerrnann, R. N., Kerr, J. M., Wang, L., and Malcolm, B. A. Simplified methods for construction, assessment and rapid screening of peptide libraries in bacteriophage. J. Mol. Biol. 227:711–718, 1992.
7. Fukuda, M. N., Ohyama, C., Lowitz, K., Matsuo, O., Pasqualini, R., Ruoslahti, E., and Fukuda, M. A peptide mimic of E-selectin ligand inhibits sialyl Lewis X-dependent lung colonization of tumor cells. Cancer Res. 60: 450–456, 2000. 8 Grant, S. C., Kris, M. G., Houghton, A. N., Chapman, P. B. (1999). Long survival of patients with small cell lung cancer after adjuvant treatment with the anti-idiotypic antibody BEC2 plus bacillus calmette-guerin. Clin. Cancer Res. 5, 1319–1323.
9. Hsuch, E. C. Tumour cell-based vaccines for the treatment of melanoma. Biodrugs. 15:713–720,2001.
10. Ishikawa, D., Kikkawa, H., Ogino, K., Hirabayashi, Y., Oku, N., and Taki, T. GD1alpha-replica peptides functionally mimic GD1alpha, an adhesion molecule of metastatic tumor cells, and suppress the tumor metastasis. FEBS Lett. 441:20–24. 1998.
11. Lesinski, G B., Smithson, S L., Srivastava, N., Chen, D., Widera, G., and Westerink, Mass. A DNA vaccine encoding a peptide mimic of Streptococcus pneumoniate serotyp 4 capsular polysaccharide induces specific anti-carbohydrate antibodies in Balb/c mice. Vaccine. 19, 1717–26 (2001).
12. Luo, P., Canziani, G., Cunto-Amesty, G., and Kieber-Emmons, T. A molecular basis for functional peptide mimicry of a carbohydrate antigen. J Bio Chem. 275, 16146–54 (2000).
13. McCaffer, M., Yao, T. J., Williams, L., Livingston, P. O., Houghton, A. N., Chapman, P. B. (1996). Immunization of melanoma patients with BEC2 anti-idiotypic monoclonal antibody that mimics GD3 ganglioside: enhanced immunogenicity when combined with adjuvant. Clin. Cancer Res. 2, 679–686.
14. Park, B. W., Zhang, H. T., Wu, C., Berezov, X., Dua, R., Wang, Q., Kao, G., O'Rourke, D. M., Green, M. I., and Murali, R. Rationally designed anti-HER2/neu peptide mimetic disables P185HER2/neu tryosine kinases in vitro and in vivo. Nature Biotechnol. 18:194–198, 2000.
15. Qiu, J., Luo, P., Wasmund, K., Steplewski, Z., and Kieber-Emmons, T. Towards the development of peptide mimotopes of carbohydrate antigens as cancer vaccines. Hybridoma. 18, 103–112 (1999).
16. Regenmortel, M. Antigenicity and immunogenicity of synthetic peptides. Biol. 29:209–213, 2001.

17. Scott, J. K. and Smith, G. P. Searching for peptide ligands with an epitope library. Science. 249:386–390, 1990.
18. Takahashi, T., Johnson, T. D., Nishinaka, Y., Morton, D. L., and Irie, R. F. IgM anti-ganglioside antibodies induced by melanoma cell vaccine with survival of melanoma patients. J. Investig. Dermatol. 112:205–209, 1999.
19. Valadon, P. and Scharff, M. D. Enhancenment of ELISAs for screening peptides in epitope phage display libraries. J. Immunol. Methods 197:171–179, 1996.
20. Wang, X., Luo, W., Foon, K. A., and Ferrone, S. Tumor associated antigen (TAA) mimicry and immunotherapy of malignant diseases from anti-idiotypic antibodies to peptide mimics. Cancer Chemother. Biol. Response Modif. 19:309–326, 2001.
21. Yao, T. J., Meyers, M., Livingston, P. O., Houghton, A. N., Chapman, P. B. (1999). Immunization of melanoma patients with BEC2-keyhose limpet hemocyanin plus BCG intradermally followed by intravenous booster immunizations with BEC2 to induce anti-GD3 ganglioside antibodies. Clin. Cancer Res. 5, 77–81.

What is claimed is:

1. An isolated and purified peptide which blocks the binding of an anti-GD3 antibody to a tumor cell expressing GD3 ganglioside and is capable of eliciting antibodies reactive against GD3 ganglioside, wherein the sequence of the peptide is SEQ ID NO:6.

2. An antigenic composition comprising a peptide which blocks the binding of an anti-GD3 antibody to a tumor cell bearing GD3 ganglioside and is capable of eliciting antibodies reactive against GD3 ganglioside and a pharmaceutically acceptable carrier, wherein the sequence of the peptide is SEQ ID NO:6.

3. The antigenic composition of claim 2 further comprising an adjuvant.

* * * * *